US011324766B2

(12) United States Patent
Morrow et al.

(10) Patent No.: US 11,324,766 B2
(45) Date of Patent: *May 10, 2022

(54) 2'-FUCOSYLLACTOSE FOR THE PREVENTION AND TREATMENT OF CORONAVIRUS-INDUCED INFLAMMATION

(71) Applicant: Glycosyn LLC, Waltham, MA (US)

(72) Inventors: Ardythe L. Morrow, Cincinnati, OH (US); David S. Newburg, Newtonville, MA (US); John M. McCoy, Reading, MA (US)

(73) Assignee: Glycosyn LLC, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/320,003

(22) Filed: May 13, 2021

(65) Prior Publication Data

US 2021/0353653 A1 Nov. 18, 2021

Related U.S. Application Data

(60) Provisional application No. 63/024,473, filed on May 13, 2020.

(51) Int. Cl.
| | |
|---|---|
| *A61K 31/702* | (2006.01) |
| *A61K 9/00* | (2006.01) |
| *A61K 45/06* | (2006.01) |
| *A61K 35/745* | (2015.01) |
| *A61K 35/742* | (2015.01) |
| *A61K 35/74* | (2015.01) |
| *A23L 33/125* | (2016.01) |
| *A23L 33/00* | (2016.01) |
| *A23L 2/52* | (2006.01) |
| *A61K 35/747* | (2015.01) |

(52) U.S. Cl.
CPC ............ *A61K 31/702* (2013.01); *A23L 2/52* (2013.01); *A23L 33/125* (2016.08); *A23L 33/40* (2016.08); *A61K 9/0056* (2013.01); *A61K 9/0095* (2013.01); *A61K 35/74* (2013.01); *A61K 35/742* (2013.01); *A61K 35/745* (2013.01); *A61K 35/747* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 7,893,041 B2 | 2/2011 | Morrow et al. | |
| 8,277,835 B2 | 10/2012 | Boehm et al. | |
| 2009/0047272 A1* | 2/2009 | Appelbaum | A61P 31/14 424/94.61 |
| 2016/0287618 A1 | 10/2016 | Sprenger et al. | |
| 2017/0081353 A1 | 3/2017 | McCoy et al. | |
| 2017/0136049 A1 | 5/2017 | Newburg et al. | |
| 2017/0306373 A1 | 10/2017 | Heidtman et al. | |
| 2018/0036327 A1* | 2/2018 | McConnell | A61K 31/702 |
| 2019/0218582 A1 | 7/2019 | Mallipeddi et al. | |
| 2019/0255083 A1 | 8/2019 | Newburg et al. | |
| 2020/0080119 A1 | 3/2020 | Merighi et al. | |
| 2020/0087691 A1 | 3/2020 | Heidtman et al. | |
| 2020/0190548 A1 | 6/2020 | Merighi et al. | |

FOREIGN PATENT DOCUMENTS

| | | |
|---|---|---|
| WO | 2013032674 A1 | 3/2013 |
| WO | 2019106620 A1 | 6/2019 |
| WO | 2019121929 A1 | 6/2019 |

OTHER PUBLICATIONS

Anand et al. (Sep. 2018) "Diet, Microbiota and Gut- Lung Connection", Frontiers in Microbiology, 9:2147 (12 pages).
Azzouz et al. (Jul. 2019) "Lupus Nephritis is Linked to Disease-Activity Associated Expansions and Immunity to a Gut Commensal", Annals of the Rheumatic Diseases, 78(7):947-956.
Bode Lars (Sep. 2012) "Human Milk Oligosaccharides: Every Baby Needs a Sugar Mama", Glycobiology, 22(9):1147-1162.
Bogiaizi et al (2018) "Metabolic Products of the Intestinal Microbiome and Extremes of Atherosclerosis", Atherosclerosis, 273:91-97 (31 pages).
Brandsma et al. (Jan. 4, 2019) "A Proinflammatory Gut Microbiota Increases Systemic Inflammation and Accelerates Atherosclerosis", Circulation Research, 124(1):94-100.
Chaturvedi et al. (Jun. 2001) "Fucosylated Human Milk Oligosaccharides Vary Between Individuals and Over the Course of Lactation", Glycobiology, 11(5):365-372.
Chaturvedi et al. (2001) "Survival of Human Milk Oligosaccharides in the Intestine of Infants", Advances in Experimental Medicine and Biology, 501:315-323.
Chen et al. (2018) "Inflammatory Responses and Inflammation-Associated Diseases in Organs", Oncotarget, 9 (6):7204-7218.
Chen et al. (Mar. 3, 2020) "The SARS-CoV-2 Vaccine Pipeline: An Overview", Current Tropical Medicine Reports, 4 pages.
Chu et al. (Apr. 2, 2018) "Gut Microbiota in Multiple Sclerosis and Experimental Autoimmune Encephalomyelitis: Current Applications and Future Perspectives", Mediators of Inflammation, 2018:8168717 (17 pages).
Cummings et al. (2015) "DC-SIGN Binds 2-Fucosyl-Lactose (2FL) at Concentrations Available in Human Milk", The FASEB Journal, 29(1 Supplement): 890.10. (Abstract Only).
Grabinger et al. (Jun. 19, 2019) "Alleviation of Intestinal Inflammation by Oral Supplementation With 2-Fucosyllactose in Mice", Frontiers in Microbiology, 10:1385 (14 pages).

(Continued)

*Primary Examiner* — Dale R Miller

(74) *Attorney, Agent, or Firm* — Mintz Levin Cohn Ferris Glovsky and Popeo, P.C.; Ingrid A. Beattie

(57) ABSTRACT

The invention provides compositions and methods for utilizing oligosaccharides, such as isolated human milk oligosaccharides, to attenuate a respiratory pathogen infection-induced host inflammation and/or to promote recovery from a respiratory pathogen infection-induced host inflammation in a subject.

9 Claims, No Drawings

(56) References Cited

OTHER PUBLICATIONS

Guo et al. (2020) "The Origin, Transmission and Clinical Therapies on Coronavirus Disease 2019 (COVID-19) Outbreak—An Update on the Status", Military Medical Research, 7(1):11 (10 pages).
Hassan et al. (2020) "Coronavirus (COVID-19): A Review of Clinical Features, Diagnosis, and Treatment", Cureus, 12(3):e7355 (7 pages).
He et al. (Jan. 15, 2016) "Human Milk Components Modulate Toll-Like Receptor-Mediated Inflammation", Advances in Nutrition, 7(1):102-111.
He et al. (2016) "The Human Milk Oligosaccharide 2'-Fucosyllactose Modulates CD14 Expression in Human Enterocytes, thereby Attenuating LPS-Induced Inflammation", Gut, 65(1):33-46.
Kasper Dennis L. (2009) "A Paradigm for Commensalism: The Role of a Specific Microbial Polysaccharide in Health and Disease", Nestlé Nutrition Institute Workshop Series. Pediatric Program, 64:1-8; discussion 8-10, 251-7.
Kho et al. (Aug. 14, 2018) "The Human Gut Microbiome—A Potential Controller of Wellness and Disease", Frontiers in Microbiology, 9:1835 (23 pages).
Knip et al. (Sep. 23, 2017) "Modulation of Type 1 Diabetes Risk by the Intestinal Microbiome", Current Diabetes Reports, 17(11):105 (8 pages).
Koromyslova et al. (Aug. 2017) "Human Norovirus Inhibition by a Human Milk Oligosaccharide", Virology, 508:81-89.
Lee et al. (Jul. 2018) "Microbiome in the Gut-Skin Axis in Atopic Dermatitis", Allergy, Asthma & Immunology Research, 10(4):354-362.
Matthay et al. (Mar. 14, 2019) "Acute Respiratory Distress Syndrome", Nature Reviews. Disease Primers, 5(1):18 (22 pages).
Mazmanian et al. (May 29, 2008) "A Microbial Symbiosis Factor Prevents Intestinal Inflammatory Disease", Nature, 453(7195):620-625.
Ochoa-Repäcü araz et al. (Sep. 2010) "A Polysaccharide from the Human Commensal Bacteroides Fragilis Protects Against CNS Demyelinating Disease", Mucosal Immunology, 3(5):487-495.
Pickard et al. (Jun. 15, 2015) "Intestinal Fucose as a Mediator of Host-Microbe Symbiosis", Journal of Immunology, 194(12):5588-5593.
Rapozo et al. (Mar. 28, 2017) "Diet and Microbiota in Inflammatory Bowel Disease: The Gut in Disharmony", World Journal of Gastroenterology, 23(12):2124-2140.
Rogier et al. (Nov. 15, 2017) "Alteration of the Intestinal Microbiome Characterizes Preclinical Inflammatory Arthritis in Mice and its Modulation Attenuates Established Arthritis", Scientific Reports, 7(1):15613 (12 pages).
Ruiz-Palacios et al. (Apr. 18, 2003) "Campylobacter Jejuni binds Intestinal H(O) Antigen (Fuc alpha 1, 2Gal beta 1, 4GlcNAc), and Fucosyloligosaccharides of Human Milk Inhibit its Binding and Infection", Journal of Biological Chemistry, 278(16):14112-14120.
Sheahan et al. (Mar. 2020) "An Orally Bioavailable Broad-Spectrum Antiviral Inhibits SARS-CoV-2 and Multiple Endemic, Epidemic and Bat Coronavirus", bioRxiv, 34 pages.
Sodhi et al. (Feb. 2021) "The Human Milk Oligosaccharides 2'-Fucosyllactose and 6'-Sialyllactose Protect against the Development of Necrotizing Enterocolitis by Inhibiting Toll-like Receptor 4 Signaling", Pediatric Research, 89(1):91-101.
Stefka et al. (Sep. 9, 2014) "Commensal Bacteria Protect Against Food Allergen Sensitization", Proceedings of the National Academy of Sciences, 111(36):13145-13150.
Surana et al. (Jan. 2012) "The Yin Yang of Bacterial Polysaccharides: Lessons Learned from B. Fragilis PSA", Immunological Reviews, 245(1):13-26 (21 pages).
Thursby et al. (May 16, 2017) "Introduction to the Human Gut Microbiota", Biochemical Journal, 474(11):1823-1836.
Troy et al. (Jan. 2010) "Beneficial Effects of Bacteroides Fragilis Polysaccharides on the Immune System", Frontiers in Bioscience (Landmark Ed), 15:25-34.

Weichert et al. (Apr. 14, 2016) "Structural Basis for Norovirus Inhibition by Human Milk Oligosaccharides", Journal of Virology, 90(9):4843-4848.
Yu et al. (2012) "The Principal Fucosylated Oligosaccharides of Human Milk Exhibit Prebiotic Properties on Cultured Infant Microbiota", Glycobiology, 23(2): 169-177.
Yu et al. (Nov. 2013) "Utilization of Major Fucosylated and Sialylated Human Milk Oligosaccharides by Isolated Human Gut Microbes", Glycobiology, 23(11):1281-1292.
Zehra et al. (Feb. 2018) "Human Milk Oligosaccharides Attenuate Antigen-Antibody Complex Induced Chemokine Release from Human Intestinal Epithelial Cell Lines", Journal of Food Science, 83(2):499-508.
Zhang et al. (Feb. 25, 2020) "The Cross-Talk Between Gut Microbiota and Lungs in Common Lung Diseases", Frontiers in Microbiology, 11:301 (14 pages).
Zhao et al. (Mar. 2019)"The Gut Microbiome in Food Allergy", Annals of Allergy, Asthma & Immunology, 122 (3):276-282.
Zheng et al. (Oct. 2018) "Gut Microbiome in type 1 Diabetes: A Comprehensive Review", Diabetes/Metabolism Research and Reviews, 34(7):e3043 (9 pages).
Glossary of medical education terms, Institute of International Medical Education, http://www.iime.org/glossary.htm Accessed in Mar. 2013, 2013.
Abdul-Rasool et al. (May 25, 2010) "Understanding Human Coronavirus HCoV-NL63", The Open Virology Journal, 4:76-84.
Charlwood et al. (Sep. 1999) "A Detailed Analysis of Neutral and Acidic Carbohydrates in Human Milk", Analytical Biochemistry, 273(2):261-277.
Delmas et al. (1992) "Aminopeptidase N is a Major Receptor for the Entero-pathogenic Coronavirus TGEV", Nature, 357:417-420.
Green (2020) "Jennewein Biotechnology Flags HMOs' Potential In Inhibiting Infectious Diseases", Nutrition Insight, 2 Pages.
Hamosh M. (Feb. 2001) "Bioactive Factors In Human Milk", Pediatric Clinics of North America, 48(1):69-86.
Huang et al. (Jul. 2015) "Human Coronavirus HKU1 Spike Protein Uses O-Acetylated Sialic Acid as an Attachment Receptor Determinant and Employs Hemagglutinin-Esterase Protein as a Receptor-Destroying Enzyme", Journal of Virology, 89(14):7202-7213.
Krempl et al. (1995) "Analysis of Cellular Receptors for Human Coronavirus OC43", Advances in Experimental Medicine and Biology, 380:371-374.
Li et al. (Nov. 27, 2003) "Angiotensin-Converting Enzyme 2 is a Functional Receptor for the SARS Coronavirus", Nature, 426(6965):450-454.
Li et al. (2011) "Effects of ABO and FUT2 Genetic Transcription Absence on ABH histo-blood Group Antigen Expression in Lung Cancer Patients", Asian Pacific Journal of Cancer Prevention, 12(12):3201-3206.
Li et al. (Aug. 15, 2007) "Porcine Aminopeptidase N is a Functional Receptor for the PEDV Coronavirus", Virology, 365(1):166-172.
Liu et al. (Jun. 2015) "Receptor Usage and Cell Entry of Porcine Epidemic Diarrhea Coronavirus", Journal of Virology, 39(11):6121-6125.
Marcobal et al. (May 2010) "Consumption of Human Milk Oligosaccharides by Gut-Related Microbes", Journal of Agricultural and Food Chemistry, 58(9):5334-5340.
Martin-Sosa et al. (Jan. 2003) "Sialyloligosaccharides in Human and Bovine Milk and in Infant Formulas Variations with the Progression of Lactation", Journal of Diary Science, 86(1):52-59.
Morrow et al. (Sep. 2004) "Human Milk Oligosaccharides are Associated with Protection Against Diarrhea in Breast-Fed Infants", The Journal of Pediatrics, 145(3):297-303.
Newburg David S (Feb. 2001) "Bioactive Components of Human Milk: Evolution, Efficiency, and Protection", Advances in Experimental Medicine and Biology, 501 (1):3-10.
Newburg et al. (Aug. 2005) "Human Milk Glycans Protect Infants Against Enteric Pathogens", Annual Review of Nutrition, 25:37-58.
Newburg David S (Mar. 1999) "Human Milk Glycoconjugates that Inhibit Pathogens", Current Medicinal Chemistry, 6(2):117-127.
Newburg et al. (Mar. 1, 2004) "Innate Protection Conferred by Fucosylated Oligosaccharides of Human Milk Against Diarrhea in Breastfed Infants", Glycobiology, 14(3):253-263.

(56) References Cited

OTHER PUBLICATIONS

Newburg et al. (Jan. 2007) "Protection of the Neonate by the Innate Immune System of Developing Gut and of Human Milk", Pediatric Research, 61 (1):2-8.
Newburg et al. (1998) "Role of Human-Milk Lactadherin in Protection Against Symptomatic Rotavirus Infection", The Lancet, 351 (9110):1160-1164.
Ninonuevo et al. (Oct. 4, 2006) "A Strategy for Annotating the Human Milk Glycome", Journal of Agricultural and Food Chemistry, 54(20):7471-7480.
Parkkinen et al. (1987) "Isolation of Sialyl Oligosaccharides and Sialyl Oligosaccharide Phosphates from Bovine Colostrum and Human Urine", Methods in Enzymology, 138:289-300.
Pendu (2004) "Histo-blood Group Antigen And Human Milk Oligosaccharides: Genetic Polymorphism And Risk Of Infectious Diseases", Advances in Experimental Medicines and Biology, 554:135-43.
Prieto et al. (Jan. 24, 1997) "Expression of Human H-type a1,2-Fucosyltransferase Encoding for Blood Group H (O) Antigen in Chinese Hamster Ovary Cells. Evidence for Preferential Fucosylation and Truncation of Polylactosamine Sequences", The Journal of Biological Chemistry, 272(4):2089-2097.
Raj et al. (Mar. 14, 2013) "Dipeptidyl Peptidase 4 is a Functional Receptor for the Emerging Human Coronavirus-EMC", Nature, 495(7440):251-254.
Schultze et al. (Apr. 1992) "Bovine Coronavirus uses N-acetyl-9-O-acetylneuraminic Acid as a Receptor Determinant to Initiate the Infection of Cultured Cells", The Journal of General Virology, 73(Pt 4):901-906.
Schultze et al. (1993) "N-Acetylneuraminic Acid Plays a Critical Role for the Haemagglutinating Activity of Avian Infectious Bronchitis Virus and Porcine Transmissible Gastroenteritis Virus", Advances in Experimental Medicine and Biology, 342:305-310.
Schultze et al. (Aug. 1996) "Transmissible Gastroenteritis Coronavirus, but not the Related Porcine Respiratory Coronavirus, has a Sialic Acid (N-glycolylneuraminic Acid) Binding Activity", Journal of Virology, 70(8):5634-5637.
Shen et al. (Jul. 6, 2001) "Resolution of Structural Isomers of Sialylated Oligosaccharides by Capillary Electrophoresis", Journal of Chromatography A, 921(2):315-321.
Tresnan et al. (Dec. 1996) "Feline Aminopeptidase N Serves as a Receptor for Feline, Canine, Porcine, and Human Coronaviruses in Serogroup I", Journal of Virology, 70(12):8669-8674.
Walther et al. (Mar. 2013) "Glycomic Analysis of Human Respiratory tract Tissues and Correlation with Influenza Virus Infection", PLoS Palthogens, 9(3):e1003223 (16 pages).
Watanabe et al. (2020) "Site-specific Analysis Of The Sars-cov-2 Glycan Shield", BioRxiv preprint, 21 Pages.
Wilde et al. (2018) "Host Factors in Coronavirus Replication", Current Topics in Microbiology and Immunology, 419:1-42.
Williams et al. (Jul. 1, 1991) "Receptor for Mouse Hepatitis Virus is a Member of the Carcinoembryonic Antigen Family of Glycoproteins", Proceedings of the National Academy of Sciences, 88(13):5533-5536.
Wrapp et al. (Mar. 13, 2020) "Cryo-EM Structure of the 2019-nCoV Spike in the Prefusion Conformation", Science, 367(6483):1260-1263.
Wu et al. (Nov. 24, 2009) "Crystal Structure of NL63 Respiratory Coronavirus Receptor-binding Domain Complexed with its Human Receptor", Proceedings of the National Academy of Sciences, 106(47):19970-19974.
Yan et al. (Mar. 27, 2020) "Structural Basis for the Recognition of SARS-CoV-2 by Full-Length Human ACE2", Science, 367(6485):1444-1448.
Yang et al. (Aug. 26, 2014) "Receptor Usage and Cell Entry of Bat Coronavirus HKU4 Provide Insight into Bat-to-Human Transmission of MERS Coronavirus", Proceedings of the National Academy of Sciences, 111 (34):12516-12521.
Yeager et al. (Jun. 4, 1992) "Human aminopeptidase N is a receptor for human coronavirus 229E", Nature, 357 (6377):420-422.
Zhao et al. (2020) "Relationship between the ABO Blood Group and the COVID-19 Susceptibility", medRxiv, 18 pages.
Zhou et al. (Mar. 2020) "A Pneumonia Outbreak Associated with a New Coronavirus of Probable Bat Origin", Nature, 579(7798):270-273.

* cited by examiner

2'-FUCOSYLLACTOSE FOR THE PREVENTION AND TREATMENT OF CORONAVIRUS-INDUCED INFLAMMATION

RELATED APPLICATIONS

This application claims the benefit of U.S. Ser. No. 63/024,473 filed May 13, 2020, which is incorporated herein by reference in its entirety.

FIELD OF THE INVENTION

The invention provides compositions and methods for utilizing human milk oligosaccharides (hMOS) to prevent and/or treat a pathogenic virus-induced inflammation in a subject.

BACKGROUND OF THE INVENTION

The recent pandemic of COVID-19 infection to millions of people worldwide presents an urgent need for a treatment capable of preventing or attenuating coronavirus infection.

SUMMARY OF THE INVENTION

Some coronaviruses, such as SARS-CoV-2 (COVID-19), are known to bind to the angiotensin-converting enzyme 2 (ACE2) receptor of an animal subject for its infection, which may lead to host inflammation. The invention is based on the discovery that human milk glycans or human milk oligosaccharides (hMOS) may be used to prevent, attenuate, or treat such infection-related inflammation with at least three beneficial activities, including: 1) preventing viruses, or other respiratory pathogens, from binding to host cells or tissue; 2) reducing host inflammation by, e.g., promoting growth and/or functions of common gut commensal bacteria; and 3) directly reducing host inflammation. The compositions described herein, such as human milk oligosaccharides [e.g., 6'-sialyllactose (6'-SL), 3'-sialyllactose (3'-SL), Lacto-N-tetraose (LNT), Lacto-N-neotetraose (LNnT), 3-fucosyllactose (3-FL), Lacto-N-fucopentaose I (LNF I), Lacto-N-fucopentaose II (LNF II), Lacto-N-fucopentaose III (LNF III), Lactodifucotetraose (LDFT), Lacto-N-difucohexaose I (LDFH I), Lacto-N-difucohexaose II (LDFH II), Disialyllacto-N-tetraose (DSLNT), 3'-galactosyllactose (3'-GL), 6'-galactosyllactose (6'-GL), 4-galactosyllactose (4'-GL), etc.], are indigestible or partially indigestible (by the host), but provide health benefits to the host by at least one of multiple mechanisms, such as attenuating the binding of respiratory pathogens, such as coronaviruses, to its receptor in the respiratory system (e.g., lung and bronchi) and/or the GI tract of a subject, thus attenuating or inhibiting viral infection, reducing host inflammation by, e.g., promoting growth and/or functions of common gut commensal bacteria; or directly reducing host inflammation. In addition, the invention provides methods of using such compositions comprising at least one isolated fucosylation oligosaccharide, such as at least one isolated human milk oligosaccharide (HMO), in an amount effective to prevent, attenuate/ reduce, and/or inhibit a respiratory pathogen (such as a coronavirus) infection-related host inflammation and/or to promote recovery from a respiratory pathogen infection-related host inflammation in the respiratory system (e.g., lung and bronchi) and/or the gastrointestinal (GI) tract of a subject. Preferably, the oligosaccharide comprises at least one isolated HMO comprising 2'-fucosyllactose (2'-FL), or combinations with other hMOS described herein.

TABLE 1

HMOS names and structures

| | | |
|---|---|---|
| 2'-FL | 2'-Fucosyllactose | Fucα1,2Galβ1,4Glc |
| 3-FL | 3-Fucosyllactose | Galβ1,4↘<br>     Glc<br>Fucα1,3↗ |
| 3',-GL | 3'-galactosyllactose | Galβ1,3Galβ1,4Glc |
| 4'-GL | 4'-galactosyllactcse | Galβ1,4Galβ1,4Glc |
| 6'-GL | 6'-galactosyllactose | Galβ1,6Galβ1,4Glc |
| LDFT | Lactodifucotetraose | Fucα1,2Galβ1,4↘<br>     Glc<br>Fucα1,3↗ |
| LNT | Lacto-N-tetraose | Galβ1,3GlcNAcβ1,3Galβ1,4Glc |
| LNnT | Lacto-N-neotetraose | Galβ1,4GlcNAcβ1,3Galβ1,4Glc |
| LNF-I | Lacto-N-fucopentaose I | Fucα1,,2Galβ1,3GlcNAcβ1,3Galβ1,4Glc |
| LNT-II | Lactco-N-fucopentaose II | Galβ,3↘<br>     GlcNAcβ1,3Galβ1,4Glc |
| LNF-III | Lacto-N-fucopentaose III | Fucα1,4↗<br>Galβ1,4↘<br>     GlcNAcβ1,3Galβ1,4Glc |
| LDFH-I | Lacto-N-difucohexaose I | Fucα1,3↗<br>Fucα1,2Galβ1,3↘<br>     GlcNAcβ1,3Galβ1,4Glc |
| LDFH-II | Lacto-difucohexaose II | Fucα1,4↗<br>Galβ1,3↘<br>     GlcNAcβ1,3Galβ1,4Glc |
| 3'-SL | 3'-Sialyllactose | Fucα1,4↗   Fucα1,3↗<br>NANAα2,3Galα1,4Glc |
| 6'-SL | 6'-Sialyllactose | NANAα2,6Galβ1,4Glc |
| DSLNT | Disialyllacto-N-tetraose | NANAα2,3Galβ1,3GlcNAcβ1,3Galβ1,4Glc<br>     NANAα2,6↗ |

The compositions of the invention are administered alone or, alternatively, in conjunction with other agents for preventing, attenuating and/or treating a respiratory pathogen infection. The compositions optionally include a pharmaceutically-acceptable excipient or inactive ingredients.

In one aspect, the invention provides a composition comprising at least one isolated human milk oligosaccharide (hMOS) in an amount effective to prevent, attenuate, or treat a pathogen-induced immune response and/or to promote recovery from a pathogen-induced immune response in a subject. In some embodiments, the pathogen-induced immune response comprises an inflammation in the lung and/or the GI tract of the subject. In some embodiments, the composition comprises at least one isolated human milk oligosaccharide (HMO) comprises 2'-fucosyllactose (2'-FL). In some embodiments, the at least one isolated human milk oligosaccharide (HMO) comprises 2'-fucosyllactose (2'-FL), 6'-sialyllactose (6'-SL), 3'-sialyllactose (3'-SL), Lacto-N-tetraose (LNT), Lacto-N-neotetraose (LNnT), 3-fucosyllactose (3-FL), Lacto-N-fucopentaose I (LNF I), Lacto-N-fucopentaose II (LNF II), Lacto-N-fucopentaose III (LNF III), Lactodifucotetraose (LDFT), Lacto-N-difucohexaose I (LDFH I), Lacto-N-difucohexaose II (LDFH II), Disialyllacto-N-tetraose (DSLNT), 3'-galactosyllactose (3'-GL), 6'-galactosyllactose (6'-GL), or 4-galactosyllactose (4'-GL). In some embodiments, the composition comprises at least one isolated human milk oligosaccharide (HMO) in an amount effective to prevent, attenuate, or treat a pathogen-induced immune response and/or to promote recovery from a pathogen-induced immune response in a subject, wherein the at least one isolated human milk oligosaccharide (HMO) comprises 2'-fucosyllactose (2'-FL), wherein the pathogen-induced immune response comprises an inflammation in the lung and/or the GI tract of the subject. In some embodiments, the composition comprises at least 60%, 75%, 90%, 95%, 98%, or 99% (w/w) of 2'-FL. In some embodiments, the composition comprises between 0.01 g 2'-FL and 10 g 2'-FL per 10 grams of composition. In some embodiments, the composition (e.g., the 2'-FL) i) prevents or reduces pathogen binding to cells of the subject; ii) attenuates the pathogen-induced immune response in the subject; and/or iii) modulating host immune response antagonizing the pathogen-induced immune response in the subject.

In some embodiments, the composition further comprises an additional agent capable of preventing, attenuating, or treating the pathogen-induced immune response and/or promoting recovery from a pathogen-induced immune response in the subject. In some embodiments, the additional agent comprises at least one of 6'-sialyllactose (6'-SL), 3'-sialyllactose (3'-SL), Lacto-N-tetraose (LNT), Lacto-N-neotetraose (LNnT), 3-fucosyllactose (3-FL), Lacto-N-fucopentaose I (LNF I), Lacto-N-fucopentaose II (LNF II), Lacto-N-fucopentaose III (LNF III), Lactodifucotetraose (LDFT), Lacto-N-difucohexaose I (LDFH I), Lacto-N-difucohexaose II (LDFH II), Disialyllacto-N-tetraose (DSLNT), 3'-galactosyllactose (3'-GL), 6'-galactosyllactose (6'-GL), or 4-galactosyllactose (4'-GL). In some embodiments, the additional agent comprises at least one of non-HMO prebiotic agents, such as galacto-oligosaccharides (GOS) or fructo-oligosaccharides (FOS), at least one probiotic bacterium (e.g., bacterium of the genera *Bifidobacterium, Lactobacillus, Lactococcus, Leuconostoc, Pediococcus, Enterococcus, Streptococcus, Bacteroides, Parabacteroides, Prevotella* or *Clostridium*), and/or at least one agent selected from the group consisting of antibiotics or anti-viral compounds, anti-inflammatory compounds, natural or synthetic corticosteroids, cortisone, hydrocortisone, bethamethasone, prednisone, prednisolone, methylprednisolone, dexamethasone, triamcinolone, nonsteroidal anti-inflammatory drugs (NSAIDs), ibuprofen, naproxen, indomethacin, oxaprozin, etodolac, nabumetone, diclofenac, vimovo, anti-pyretics, paracetamol, aspirin, and acetaminophen.

In some embodiments, the composition described herein is in the form of a powder, a tablet, an aerosol, feed for mammalian animals, a packet of sugar, yogurt, a beverage, a weaning food, or an infant formula. In some embodiments, the respiratory pathogen comprises a virus. For example, the virus may comprise i) a coronavirus; ii) a severe acute respiratory syndrome virus (SARS-CoV); iii) a SARS-CoV-2 (COVID-19) virus; and/or iv) a Middle East respiratory syndrome coronavirus (MERS-Cov). In some embodiments, the virus binds to the ACE2 receptor on the animal cell or tissue. In some embodiments, the binding between the virus and the animal cell or tissue is mediated by fucosylation on the animal cell or tissue, such as at least one fucosylated oligosaccharide or one fucosylated polypeptide or protein. In some embodiments, the animal cell or tissue described herein comprises a tissue of an animal respiratory system (e.g., lung and bronchi) or the gastrointestinal (GI) tract mucosa or a cell in such tissue. For example, an animal respiratory tissue may include a tissue from at least one of the lung or the upper respiratory tract (including, e.g., nose, nasal cavities, sinuses, pharynx and the part of the larynx above the vocal folds) or the lower tract (including, e.g., the lower part of the larynx, the trachea, bronchi, bronchioles and the alveoli).

In some embodiments, the animal cell or tissue described herein expresses a fucosyltransferase 2 (FUT2) genotype.

In some embodiments, the subject is a human, non-human primate, mouse, rat, dog, cat, horse, cattle, sheep, pig, chicken, or goat.

In some embodiments, the subject is an infant, a child, an adult, and/or an elder.

In some embodiments, the subject has, is prone to have, or is specifically sensitive or vulnerable to, a disease or disorder selected from the group consisting of pneumonia, acute respiratory distress syndrome (ARDS), respiratory failure, impaired lung function, hypoxemia, systemic organ failure, infectious diarrhea, antibiotic-associated diarrhea, traveler's diarrhea, necrotizing enterocolitis, inflammatory bowel disease, and an allergy inflammation.

In another aspect, the invention provides a use of the composition described herein for preparation of a medicament for preventing, attenuating, or treating a pathogen-induced immune response and/or promoting recovery from a pathogen-induced immune response in a subject, comprising administering to the subject a pharmaceutically effective amount of at least one isolated human milk oligosaccharide (HMO) comprising 2'-fucosyllactose (2'-FL).

In another aspect, the invention provides a method of preventing, attenuating, or treating a pathogen-induced immune response and/or promoting recovery from a pathogen-induced immune response in a subject, comprising administering to the subject a pharmaceutically effective amount of at least one isolated human milk oligosaccharide (HMO) comprising 2'-fucosyllactose (2'-FL). In some embodiments, the at least one isolated HMO comprises at least 60%, 75%, 90%, 95%, 98%, or 99% (w/w) of 2'-FL. In some embodiments, the pharmaceutically effective amount is equivalent to a dosage of
  i) about 0.2 g to 10 g per day;
  ii) about 1 g to 10 g per day; and/or
  ii) about 5 g to 10 g per day.

In some embodiments, the at least one isolated HMO is administered to the lung and/or the GI tract of the subject.

In some embodiments, the method described herein further comprises administering a pharmaceutically effective amount of an additional agent capable of preventing, attenuating, or treating the pathogen-induced immune response and/or promoting recovery from a pathogen-induced immune response to the subject. In some embodiments, the additional agent comprises at least one of 6'-sialyllactose (6'-SL), 3'-sialyllactose (3'-SL), Lacto-N-tetraose (LNT), Lacto-N-neotetraose (LNnT), 3-fucosyllactose (3-FL), Lacto-N-fucopentaose I (LNF I), Lacto-N-fucopentaose II (LNF II), Lacto-N-fucopentaose III (LNF III), Lactodifucotetraose (LDFT), Lacto-N-difucohexaose I (LDFH I), Lacto-N-difucohexaose II (LDFH II), Disialyllacto-N-tetraose (DSLNT), 3'-galactosyllactose (3'-GL), 6'-galactosyllactose (6'-GL), or 4-galactosyllactose (4'-GL). In some embodiments, the additional agent comprises at least one of non-HMO prebiotic agents, such as galacto-oligosaccharides (GOS) or fructo-oligosaccharides (FOS), at least one probiotic bacterium (e.g., bacterium of the genera *Bifidobacterium, Lactobacillus, Lactococcus, Leuconostoc, Pediococcus, Enterococcus, Streptococcus, Bacteroides, Parabacteroides, Prevotella* or *Clostridium*), and/or at least one agent selected from the group consisting of antibiotics or anti-viral compounds, anti-inflammatory compounds, natural or synthetic corticosteroids, cortisone, hydrocortisone, bethamethasone, prednisone, prednisolone, methylprednisolone, dexamethasone, triamcinolone, nonsteroidal anti-inflammatory drugs (NSAIDs), ibuprofen, naproxen, indomethacin, oxaprozin, etodolac, nabumetone, diclofenac, vimovo, anti-pyretics, paracetamol, aspirin, and acetaminophen. In some embodiments, the pathogen comprises a virus comprising i) a coronavirus;
ii) a COVID-19 virus;
iii) a severe acute respiratory syndrome virus (SARS-CoV); and/or
iv) a MERS-CoV.

In some embodiments, the subject is a human, a non-human primate, mouse, rat, dog, cat, horse, cattle, sheep, pig, chicken, or goat. In some embodiments, the subject has, is prone to have, or is specifically sensitive or vulnerable to, a disease or disorder selected from the group consisting of pneumonia, acute respiratory distress syndrome (ARDS), respiratory failure, impaired lung function, hypoxemia, systemic organ failure, infectious diarrhea, antibiotic-associated diarrhea, traveler's diarrhea, necrotizing enterocolitis, inflammatory bowel disease, and an allergy inflammation.

In some embodiments, the method described herein comprising administering the composition to the respiratory system (e.g., lung and bronchi) or the gastrointestinal (GI) tract mucosa of the subject. In some embodiments, the at least one isolated HMO described herein is administered to the subject through an acceptable routes, such as inhalation, pulmonary lavage, oral ingestion, anal administration, and/or injection. In some embodiments, the pharmaceutically effective amount for the at least one isolated HMO described herein is equivalent to a dosage of i) about 0.2 g to 10 g per day; ii) about 1 g to 10 g per day; and/or ii) about 5 g to 10 g per day. In some embodiments, the pharmaceutically effective amount for the at least one isolated HMO described herein is equivalent to a dosage of about 0.2 g to about 10 g per day, about 0.5 g to about 10 g per day, about 1 g to about 10 g per day, about 1 g to about 5 g per day, about 5 g to about 10 g per day, or any dosages found effective to the specific subject.

As used herein, an "isolated" or "purified" oligosaccharide is substantially free of other oligosaccharides, with which it naturally occurs in human milk. Purified oligosaccharides are also free of cellular material when produced biosynthetically, or other chemicals when chemically synthesized. Purified compounds are at least 50% or 60% (by dry weight) of the compound of interest. Preferably, the preparation is at least 70%, 75%, 80%, 85%, 90%, 95%, 98%, 99%, or more, pure, by weight the compound of interest. For example, a purified oligosaccharide, e.g., 2'-FL, 3-FL, LDFT, or others described herein, is one that is at least 50%, 60%, 70%, 75%, 80%, 85%, 90%, 91%, 92%, 93%, 94%, 95%, 98%, 99%, or 100% (w/w) of the desired oligosaccharide by weight. Purity is measured by any appropriate standard method, for example, by column chromatography, thin layer chromatography, or high-performance liquid chromatography (HPLC) analysis. The oligosaccharides are purified and used in a number of products for consumption by humans as well as animals, such as companion animals (dogs, cats) as well as livestock (bovine, equine, ovine, caprine, or porcine animals, as well as poultry). "Purified" also defines a degree of sterility that is safe for administration to a human subject, e.g., lacking infectious or toxic agents.

Similarly, by "substantially pure" is meant an oligosaccharide that has been separated from the components that naturally accompany it. Typically, the oligosaccharide is substantially pure when it is at least 50%, 60%, 70%, 75%, 80%, 85%, 90%, 95%, 99%, or even more, by weight, free from the proteins and naturally-occurring organic molecules with which it is naturally associated.

The mean concentrations of 2'-FL, 3-FL, and LDFT in human milk are as follows: 2'-FL=2.43 g/L (±0.26), 3-FL=0.86 g/L (±0.10), and LDFT=0.43 g/L (±0.04; Chaturvedi P, et al. 2001 Glycobiology, May; 11(5):365-72). Thus, the mean ratio of 2'-FL:3FL:LDFT in human milk is 5.65:2:1. To form compositions comprising more than one isolated oligosaccharide, e.g., a composition comprising two isolated oligosaccharides, the first oligosaccharide (e.g., 2'-FL, 3-FL, or LDFT) and the second oligosaccharide may be mixed in any ratio described herein. In some embodiments, the composition comprises the first purified oligosaccharide (e.g., 2'-FL, 3-FL, or LDFT) and the second oligosaccharide in a ratio of, e.g., 1:1, 1:2, 1:5, 1:10, 1:100, 100:1, 10:1, 5:1, or 2:1, or any other ratio suitable to obtain prebiotic effects.

In some embodiments, the subject is pre-treated with at least one agent for preventing the respiratory pathogen infection (e.g., an antibiotic). Such antibiotics may include, for example, at least one of Kanamycin, Gentamicin, Colistin, Metronidazole, Vancomycin, or any such agents or antibiotics known by a skilled artisan with such function.

In some embodiments, the at least one isolated HMO attenuates the respiratory pathogen infection, measurable by, e.g., pathogen colonization and/or adhesiveness, to cells or tissue of the subject. In some embodiments, the at least one isolated HMO attenuates the pathogen infection, e.g., the pathogen colonization and/or adhesiveness to cells or tissue of the subject by at least 20%, 30%, 40%, 50%, 60%, 65%, 70%, 75%, 80%, 85%, 90%, 95%, or more.

The at least one isolated HMO described herein may comprise 2'-FL, 3-FL, 6'-SL, 3'-SL, LNFPI, TFiLNO, or other oligosaccharides. In some embodiments, the at least one isolated HMO comprises 2'-FL. In some embodiments, the at least one isolated HMO is at least 50%, 60%, 70%, 80%, 90%, 95%, 99%, or more pure (in, e.g., w/w).

In some embodiments, the concentration by weight of the at least one isolated HMO in the composition is i) from about 1% to about 99%; ii) from about 10% to about 90%; iii) from about 30% to about 70%; iv) from about 40% to about 60%; or v) about 50%.

In some embodiments, the composition described herein may include a $2^{nd}$, $3^{rd}$, $4^{th}$, $5^{th}$, $6^{th}$, $7^{th}$, $8^{th}$, $9^{th}$, or $10^{th}$ purified oligosaccharide (concentration by weight as described above).

In some embodiments, the composition described herein comprises between 0.01 g and 10 g of the first purified oligosaccharide, e.g., 2'-FL, 3-FL, LDFT, or others described herein, per 10 grams of composition. For example, the composition comprises between 0.1 g and 5 g, between 0.5 g and 5 g, between 1 g and 5 g, or between 1.5 g and 3 g of the at least one isolated oligosaccharide, e.g., 2'-FL, 3-FL, LDFT, or others described herein, per 10 grams of composition. In some embodiments, the composition comprises between 0.01 g and 1 g of the at least one isolated oligosaccharide per gram of composition. In some embodiments, the composition comprises between 0.01 g 2'-FL and 1 g 2'-FL per gram of composition.

In some embodiments, the composition described herein comprises a second oligosaccharide, in addition to the at least one isolated oligosaccharide in the composition. In some embodiments, the second oligosaccharide is a purified human milk oligosaccharide. In some embodiments, the second oligosaccharide is not a human milk oligosaccharide. In some embodiments, the second oligosaccharide comprises fructo-oligosaccharides (FOS), galacto-oligosaccharides (GOS), or lactulose. In some embodiments, the second oligosaccharide comprises galacto-oligosaccharides (GOS).

The subject described herein may be a mammal. In some embodiments, the subject is a human. In some embodiments, the subject is a non-human mammal. In some embodiments, the subject is a pre-term infant, a term infant, a child, an adolescent, or an elder.

The composition described herein is in the form of a tablet, a capsule, a powder, a beverage, or an infant formula. For example, the at least one isolated oligosaccharide (such as HMO) of the invention are in the form of powdered/dry milk. By "infant" is meant a child under the age of 12 months. By "infant formula" is meant a foodstuff intended for particular nutritional use by infants aged under twelve months and constituting the principal liquid element in the progressively diversified diet of this category of person. In some embodiments, the composition described herein is provided in dry milk, in mashed rice, in a banana, in a porridge, or in a gruel. Due to the surge in disease in infants at weaning, the HMOS of the invention are added to weaning foods (e.g., mashed rice, bananas, porridges and other gruels, formula, etc.) to reduce or ameliorate these diseases. Optionally, the HMOS described herein are added to the weaning foods during the manufacturing process. Alternatively, the HMOS are added to the weaning foods after the manufacturing process, but prior to ingestion. For example, packets of sugars including one or more isolated or purified HMOS are added to weaning foods prior to infant ingestion.

The composition described herein may be also added to other consumable products such as yogurt or probiotic beverages for consumption by infants, children, and adults. For example, the composition may be added to powdered/dry milk.

The composition described herein may be administered to the subject locally or systemically through other viable routes to the respiratory system or the GI tract.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

By the terms "effective amount" and "therapeutically effective amount" of a formulation or formulation component is meant a sufficient amount of the formulation or component to provide the desired effect. For example, by "an effective amount" is meant an amount of an oligosaccharide to prevent, attenuate, and/or inhibit, a respiratory pathogen-induced host inflammation in a subject, or to treat a respiratory pathogen-induced host inflammation in a subject. Ultimately, the attending physician or veterinarian decides the appropriate amount and dosage regimen.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

DETAILED DESCRIPTION

Some respiratory pathogens, such as coronaviruses, infect millions of people and cause enormous mobility and mortality. The health of individuals, especially the pathogen-induced inflammation in these individuals, depends on individual age, disease, microorganism infection, stress, nutritional components, and pharmaceutical treatments.

Described herein are compositions that contain at least one fucosylated oligosaccharide, such as at least one isolated human milk oligosaccharide (hMOS), in an amount effective to prevent, attenuate/reduece, and/or inhibit a respiratory pathogen infection-induced inflammation and/or to promote recovery from the pathogen infection-induced inflammation in the respiratory system and/or the GI tract of a subject. Such fucosylated oligosaccharides include, e.g., 2'-fuco syllactose (2'-FL), 3-fucosyllactose (3-FL), lactodifucotetraose (LDFT), and others described herein. The compositions described herein prevent, attenuate, and/or inhibit the binding, and thus the entry for infection, of the pathogen (or other pathogens) to a cell or tissue of the respiratory system and/or the GI tract of the subject, promoting growth and/or functions of common gut commensal bacteria, and/or directly regulating (e.g., reducing) host immune responses. Not intended to be limiting, the binding and/or the infection require fucosylation on the cell or tissue, while the compositions described herein compete with endogenous receptors for the pathogen (or other pathogens) to bind the pathogen (or other pathogens), thus preventing, attenuating or inhibiting the pathogen (or other pathogens) from binding to the cell or tissue and causing infection.

As described in details below, at least one isolated human milk oligosaccharide (HMO) is administrated in an amount effective to prevent, attenuate or inhibit a respiratory pathogen (e.g., a coronavirus) infection-induced host inflammation and/or to promote recovery from a respiratory pathogen infection-induced host inflammation in the respiratory system and/or the gastrointestinal (GI) tract of a subject. For example, as described in detail below, at least one isolated and/or purified 2'-FL, 3-FL, LDFT, or other hMOS, is administrated to selectively prevent, attenuate or inhibit binding of the pathogen to its receptor in the respiratory system and/or the GI tract of the subject, to improve growth and/or functions of common gut commensal bacteria, and/or to directly regulate (e.g., reduce) host immune responses.

Respiratory Pathogens

Multiple pathogens may infect the respiratory system and/or the GI tract of a subject described herein. For example, SARS-CoV, SARS-CoV-2, and hCoV-NL63, are known respiratory pathogens.

Coronaviruses are a group of related RNA viruses that cause diseases in mammals and birds. In humans, these viruses cause respiratory tract infections that can range from mild to lethal. Mild illnesses include some cases of the common cold (which is caused also by certain other viruses, predominantly rhinoviruses), while more lethal varieties can cause SARS, MERS, and COVID-19. Symptoms in other species vary: in chickens, they cause an upper respiratory tract disease, while in cows and pigs they cause diarrhea.

SARS-CoV-2/COVID-19

In 2019 an outbreak of acute respiratory illness in Wuhan, China, lead to the discovery of a novel zoonotic coronavirus closely related to the previously identified severe acute respiratory syndrome virus (SARS-CoV). The novel virus was named SARS-CoV-2, and the disease it causes in humans was given the name COVID-19 [Guo, Y. R., et al., The origin, transmission and clinical therapies on coronavirus disease 2019 (COVID-19) outbreak—an update on the status. *Mil Med Res*, 2020. 7(1): p. 11; Hassan, S. A., et al., Coronavirus (COVID-19): A Review of Clinical Features, Diagnosis, and Treatment. *Cureus*, 2020.]. In the early weeks of 2020 SARS-CoV-2/COVID-19 radiated from China and became a global pandemic.

In approximately 80% of COVID-19 patients, symptoms are relatively mild, flu-like and self-resolving. These symptoms include fever, cough, sore throat, fatigue, and head and/or muscle aches. However, around 20% of COVID-19 patients progress to exhibit more serious pulmonary issues, including shortness of breath, pneumonia, and acute respiratory distress syndrome (ARDS). Respiratory failure from ARDS is the leading cause of COVID-19 mortality, which overall lies between 2 and 5% of cases.

ARDS [Matthay, M. A., et al., Acute respiratory distress syndrome. *Nat Rev Dis Primers*, 2019. 5(1): p. 18.] is characterized by an acute progressive inflammatory reaction in the lungs, which in the case of COVID-19 is brought on by the ongoing SARS-CoV-2 infection. The lung inflammatory reaction in response to infection leads to excessive fluid build-up, with consequent impaired pulmonary function and hypoxemia. Ongoing neutrophil and T-lymphocyte infiltration into the infected lung tissue amplifies the inflammation which can lead to a "cytokine storm", i.e. an uncontrolled release of proinflammatory cytokines, leading to profound pulmonary damage, systemic organ failure, and death.

The SARS-CoV-2 virus is novel and much remains unknown about its biology. Prevention and treatment strategies for COVID-19 are in their infancy, with many ongoing approaches [Knip, M. and J. Honkanen, Modulation of Type 1 Diabetes Risk by the Intestinal Microbiome. *Curr Diab Rep*, 2017. 17(11): p. 105] aimed at preventing or reducing the incidence and extent of SARS-CoV-2 infection, e.g. through the development of SARS-CoV-2 vaccines [Chen, W. H., et al., The SARS-CoV-2 Vaccine Pipeline: an Overview. *Curr Trop Med Rep*, 2020: p. 1-4] or SARS-CoV-2-targeted anti-viral agents [Sheahan, T. P., et al., An orally bioavailable broad-spectrum antiviral inhibits SARS-CoV-2 and multiple endemic, epidemic and bat coronavirus. *bioRxiv*, 2020]. However, there is also a need for additional approaches aimed at preventing or mitigating the damaging inflammatory reaction which causes much of the serious morbidity and mortality associated with COVID-19.

Inflammation

The human immune system is exquisitely sensitive to the presence of microbial and viral pathogens, and possesses highly-evolved innate and acquired mechanisms for recognizing molecular signatures of infection, such as the presence of bacterial cell wall components, bacterial and viral nucleic acid fragments, or specific pathogen antigens seen previously in prior infections. The immune system is also powerfully triggered by the presence of dead or dying infected host cells.

After an infection is detected, the human host orchestrates a vigorous response to eliminate invading pathogens and to develop future immunity Inflammation is an integral part of this response [Chen, L., et al., Inflammatory responses and inflammation-associated diseases in organs. *Oncotarget*, 2018. 9(6): p. 7204]. Pro-inflammatory cytokines are released and blood vessel tight junctions loosen to allow plasma, plasma factors, antibodies, and activated immune cells access into infected tissues where pathogen neutralization can occur. This is followed by clearance of both inactivated pathogens and necrotic tissue, and finally by initiation of tissue repair processes. While this well-controlled inflammatory response is essential and highly protective, an uncontrolled inflammatory response can be very destructive, and in extreme cases is life-threatening.

The Microbiota and Inflammation

In recent years the advent of high throughput DNA sequencing technology has led to an explosion in understanding of the composition and functions of the human gut microbiota [Kho, Z. Y. and S. K. Lal, The Human Gut Microbiome—A Potential Controller of Wellness and Disease. *Front Microbiol*, 2018. 9: p. 1835; Thursby, E. and N. Juge, Introduction to the human gut microbiota. *Biochem J*, 2017. 474(11): p. 1823-18363]. Disorders of the gut ecosystem (gut dysbiosis) have been linked to gut inflammatory diseases [Rapozo, D. C. M., C. Bernardazzi, and H. S. P. de Souza, Diet and microbiota in inflammatory bowel disease: The gut in disharmony. *World J Gastroenterol*, 2017. 23(12): p. 2124-2140], and modulations of the gut microbiota have been shown to alleviate gut inflammation (Grabinger, T., et al., Alleviation of Intestinal Inflammation by Oral Supplementation With 2-Fucosyllactose in Mice. *Front Microbiol,* 2019. 10: p. 1385). The gut microbiota has also been linked to the functioning of distal organ systems, and gut dysbiosis has been tied into many diseases, including many with systemic inflammatory involvement. Examples of this include; inflammatory arthritis [Rogier, R., et al., Alteration of the intestinal microbiome characterizes preclinical inflammatory arthritis in mice and its modulation attenuates established arthritis. *Sci Rep,* 2017. 7(1): p. 15613], atherosclerosis [Brandsma, E., et al., A Proinflammatory Gut Microbiota Increases Systemic Inflammation and Accelerates Atherosclerosis. *Circ Res,* 2019. 124(1): p. 94-100; Bogiatzi, C., et al., Metabolic products of the intestinal microbiome and extremes of atherosclerosis. *Atherosclerosis,* 2018. 273: p. 91-97], atopic dermatitis [Lee, S. Y., et al., Microbiome in the Gut-Skin Axis in Atopic Dermatitis. *Allergy Asthma Immunol Res,* 2018. 10(4): p. 354-362] and allergy [Zhao, W., H.-E. Ho, and S. Bunyavanich, The gut microbiome in food allergy. *Ann Allergy Asthma Immunol,* 2019. 122(3): p. 276-282; Stefka, A. T., et al., Commensal bacteria protect against food allergen sensitization. *Proc Natl Acad Sci USA,* 2014. 111(36): p. 13145-50.], lupus (Azzouz, D., et al., Lupus nephritis is linked to disease-activity associated expansions and immunity to a gut commensal. *Ann Rheum Dis,* 2019), multiple sclerosis (Ochoa-Repáraz, J., et al., A polysaccharide from the human commensal *Bacteroides fragilis* protects against CNS demyelinating disease. *Mucosal Immunol,* 2010. 3(5): p. 487-95; Chu, F., et al., Gut Microbiota in Multiple Sclerosis and Experimental Autoimmune Encephalomyelitis: Current Applications and Future Perspectives. *Mediators Inflamm,* 2018. 2018: p. 8168717) and type 1 diabetes [Zheng, P., Z. Li, and Z. Zhou, Gut microbiome in type 1 diabetes: A comprehensive review. *Diabetes Metab Res Rev,* 2018. 34(7): p. e3043]. In particular it has been found that there is cross-talk between the lungs and the gut (the "lung-gut axis") (Zhang, D., et al., The Cross-Talk Between Gut Microbiota and Lungs in Common Lung Diseases. *Front Microbiol,* 2020. 11: p. 301; Anand, S. and S. S. Mande, Diet, Microbiota and Gut-Lung Connection. *Front Microbiol,* 2018. 9: p. 2147) and gut disturbances have been noted that accompany many lung diseases (Zhang et al. 2020).

Human Milk Glycans or Human Milk Oligosaccharides (HMOs)

Human milk oligosaccharides (hMOS) are a diverse set of several hundred sugar molecules found in human milk that play an important role in ensuring the health and development of the growing infant [Bode, L., Human milk oligosaccharides: Every baby needs a sugar mama. *Glycobiology,* 2012. 22(9): p. 1147-62]. hMOS are built on a lactose framework, and range in size from 3 to approximately 20 sugar units (and beyond). Their molecular structures comprise various combinations of the monosaccharides fucose, galactose, glucose, N-acetyl-glucosamine and sialic acid. hMOS are absorbed poorly by the infant gut wall [Chaturvedi, P., et al., Survival of human milk oligosaccharides in the intestine of infants. *Adv Exp Med Biol,* 2001. 501: p. 315-23] and are consequently the majority are retained in the gut lumen, where they are utilized by the resident microbiota as a carbon source for growth (i.e. hMOS are natural human prebiotics) [Yu, Z.-T., et al., The Principal Fucosylated Oligosaccharides of Human Milk Exhibit Prebiotic Properties on Cultured Infant Microbiota. *Glycobiology,* 2012. 23(2): p. 169-77]. It is thought that, though breast feeding, hMOS in mother's milk guide the early colonization of the infant gut by hMOS-utilizing commensal organisms, leading to the installation of a balanced gut ecosystem that promotes good health and that is resistant to colonization by pathogens.

A distinguishing feature of gut commensals over other microorganisms is that they have co-evolved to exist peaceably with their host, and in particular with their host's immune system. The multiple billions of commensal bacteria living in the gastrointestinal tract of a healthy individual do not trigger the powerful host immune and inflammatory responses that typically detect, kill and eliminate invading bacteria. The reasons for this are not yet fully understood, however it is known that certain commensal bacteria have developed ways to induce the host to down-regulate immune responses [Mazmanian, S. K., J. L. Round, and D. L. Kasper, A microbial symbiosis factor prevents intestinal inflammatory disease. *Nature,* 2008. 453(7195): p. 620-5; Kasper, D. L., A paradigm for commensalism: the role of a specific microbial polysaccharide in health and disease. Nestle Nutr Workshop Ser Pediatr Program, 2009. 64: p. 1-8, discussion 8-10, 251-7; Troy, E. B. and D. L. Kasper, Beneficial effects of *Bacteroides fragilis* polysaccharides on the immune system. *Front Biosci* (Landmark Ed), 2010. 15: p. 25-34; Surana, N. K. and D. L. Kasper, The yin yang of bacterial polysaccharides: lessons learned from *B. fragilis* PSA. *Immunol Rev,* 2012. 245(1): p. 13-26]. These same commensal bacteria grow and thrive using hMOS as a carbon source (Yu, Z. T., C. Chen, and D. S. Newburg, Utilization of major fucosylated and sialylated human milk oligosaccharides by isolated human gut microbes. *Glycobiology,* 2013).

2'-Fucosyllactose (2'-FL)

2'-fucosyllactose (2'-FL) is one of the simplest hMOS, being a trisaccharide with an α(1,2)-linked fucose bound to the galactose moiety of lactose (Bode 2012). 2'-FL is, by far, the most abundant single hMOS component in the milk of most mothers, representing approximately 25% of the total oligosaccharide content by weight. As the most abundant hMOS, 2'-FL is perhaps the most well-studied, and was the first hMOS molecule produced in bulk for inclusion in infant formula and foodstuffs. 2'-FL may have three broad classes of beneficial activities towards host inflammation induced by respiratory pathogen infection:

1) α(1,2)-fucose-conjugated glycans on epithelial surfaces are well established as being binding sites for a variety of pathogens, principally in the gut. For example, *Campylobacter jejuni, Salmonella typhimurium, Helicobacter pylori,* enterotoxigenic *Escherichia coli, Vibrio cholerae,* and Norovirus all bind to α(1,2)-fucose-conjugated epithelial glycans at the first step in infection [Pickard, J. M. and A. V. Chervonsky, Intestinal fucose as a mediator of host-microbe symbiosis. *J Immunol,* 2015. 194(12): p. 5588-93]. 2'-FL comprises an α(1,2)-linked fucose moiety, and has been shown to act as a soluble "decoy" molecule (competitive inhibitor) that can effectively prevent pathogen binding [Ruiz-Palacios, G. M., et al., *Campylobacter jejuni* binds intestinal H(O) antigen (Fuc alpha 1, 2Gal beta 1, 4GlcNAc), and fucosyloligosaccharides of human milk inhibit its binding and infection. *J Biol Chem,* 2003. 278 (16): p. 14112-20; Koromyslova, A., et al., Human norovirus inhibition by a human milk oligosaccharide. *Virology,* 2017. 508: p. 81-89; Weichert, S., et al., Structural Basis for Norovirus Inhibition by Human Milk Oligosaccharides. *J Virol,* 2016];

2) 2'-FL is a prebiotic sugar that is efficiently utilized for growth by common gut commensal bacteria such as the Bifidobacteria and the *Bacteroides* (Yu et al., 2012; Yu et al., 2013). Certain gut commensals that grow on 2'-FL (e.g. *Bacteroides fragilis*) have also been shown to possess mechanisms for down-regulating inflammation in the gut (Mazmanian et al., 2008; Kasper et al., 2009; Troy and Kasper, 2010; Surana and Kasper, 2012) (i.e., 2'-FL has an indirect anti-inflammatory activity that is mediated by the gut microbiota); and 3) 2'-FL has been shown to have direct effects on immune function [He, Y., et al., The human milk oligosaccharide 2'-fucosyllactose modulates CD14 expression in human enterocytes, thereby attenuating LPS-induced inflammation. *Gut*, 2016. 65(1): p. 33-46; Sodhi, C. P., et al., The human milk oligosaccharides 2'-fucosyllactose and 6'-sialyllactose protect against the development of necrotizing enterocolitis by inhibiting toll-like receptor 4 signaling. *Pediatric Research*, 2020: p. 1-13; He, Y., N. T. Lawlor, and D. S. Newburg, Human Milk Components Modulate Toll-Like Receptor-Mediated Inflammation. *Adv Nutr*, 2016. 7(1): p. 102-11; Zehra, S., et al., Human Milk Oligosaccharides Attenuate Antigen-Antibody Complex Induced Chemokine Release from Human Intestinal Epithelial Cell Lines. *J Food Sci*, 2018; Cummings, R., et al., *DC-SIGN Binds 2-Fucosyl-Lactose (2FL) at Concentrations Available in Human Milk The FASEB Journal*, 2015. 29(1 Supplement): p. 890-10].

2'-Fucosyllactose for the Prevention and Treatment of Coronavirus-Induced Inflammation Much of the serious morbidity and mortality caused by SARS-CoV-2 infection is a result of an uncontrolled inflammatory reaction in the lungs. Mitigating or preventing this severe inflammatory reaction would be expected to impact favorably the clinical course of COVID-19 disease, and save many lives.

2'-FL has been shown to have a direct anti-inflammatory activity, and, moreover, exhibits an indirect anti-inflammatory activity mediated by the microbiota. Modulating the microbiota has previously been shown to have impacts on systemic inflammation in multiple disease scenarios. The present invention envisages the use of 2'-FL as an agent to prevent or reduce the inflammation (principally in the lungs) caused by SARS-CoV-2 infection. 2'-FL may be administered orally, either by itself in tablet or powder form, or it may be conveniently dissolved in a little water or other beverage, or it may be included in foodstuffs or in food or medical supplements. The preferred 2'-FL adult dose is 5 g per day, but anywhere between 0.2 g per day up to 10 g per day may be taken. 2'-FL is a natural component of human milk and as such it is non-toxic, however high doses (i.e. >10 g per day) may lead to mild gut discomfort and a reversible osmotic diarrhea. 2'-FL may be taken at the onset of COVID-19 symptoms, or may be safely taken daily as a prophylactic during times when COVID-19 is prevalent in populations.

2'-FL may be combined with other agents, for example other human milk oligosaccharides that may exhibit direct or indirect anti-inflammatory actions may synergize with, or add to, the anti-inflammatory actions of 2'-FL. Examples of additional hMOS which could be used in combination with 2'-FL include, but are not limited to: 6'-sialyllactose (6'-SL), 3'-sialyllactose (3'-SL), Lacto-N-tetraose (LNT), Lacto-N-neotetraose (LNnT), 3-fucosyllactose (3-FL), Lacto-N-fucopentaose I (LNF I), Lacto-N-fucopentaose II (LNF II), Lacto-N-fucopentaose III (LNF III), Lactodifucotetraose (LDFT), Lacto-N-difucohexaose I (LDFH I), Lacto-N-difucohexaose II (LDFH II), Disialyllacto-N-tetraose (DSLNT), 3'-galactosyllactose (3'-GL), 6'-galactosyllactose (6'-GL) and 4-galactosyllactose (4-GL). Other non-hMOS prebiotics, such as mixtures of synthetic galacto-oligosaccharides (GOS) or fructo-oligosaccharides (FOS) could be utilized in combination with 2'-FL to treat coronavirus-induced inflammation.

Other pharmaceutical agents may also be used in combination with 2'-FL in treating coronavirus-induced inflammation, for example antibiotics or anti-viral compounds, or other anti-inflammatory compounds such as natural or synthetic corticosteroids (e.g. cortisone, hydrocortisone, bethamethasone, prednisone, prednisolone, methylprednisolone, dexamethasone, triamcinolone), NSAIDs (nonsteroidal anti-inflammatory drugs, e.g. ibuprofen, naproxen, indomethacin, oxaprozin, etodolac, nabumetone, diclofenac, vimovo), and other anti-pyretics (e.g. paracetamol, aspirin, acetaminophen).

2'-FL may also be used to combat inflammation resulting from SARS-CoV-2 infection in combination with pre-, co- or post-administered probiotic organisms, for example with probiotic bacteria of the genera *Bifidobacterium, Lactobacillus, Lactococcus, Leuconostoc, Pediococcus, Enterococcus, Streptococcus, Bacteroides, Parabacteroides, Prevotella* or *Clostridium*.

2'-FL may also be utilized to treat the inflammation resulting from infections of other coronaviruses, e.g. SARS-CoV and MERS-CoV, or other viruses causing pulmonary inflammation.

Administration Routes

Pharmaceutically available and/or effective administration routes may be used to deliver the fucosylated oligosaccharides (such as HMOS) described herein to a subject. With no intention to be limiting, the fucosylated oligosaccharides may be administered locally or systemically to a subject, including administering to, e.g., the respiratory system and/or the GI tract of the subject, via, e.g., inhalation, pulmonary lavage, oral ingestion, anal administration, infusion, and/or injection. Administration routes also include, but not limited to, administering to a subject intravenously, intradermally, intraperitoneally, intrapleurally, intratracheally, intramuscularly, subcutaneously, by injection, and by infusion.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed:

1. A method of attenuating, or treating a corona virus pathogen-induced immune response and/or promoting recovery from a corona virus pathogen-induced immune response in a subject, comprising administering to the subject a composition comprising a pharmaceutically effective amount of at least one isolated human milk oligosaccharide (HMO) comprising 2'-fucosyllactose (2'-FL), wherein said at least one isolated HMO comprises at least 60%, 75%, 90%, 95%, 98%, or 99% (w/w) of 2'-FL, further wherein said corona virus is selected from the group consisting of i) a COVID-19 virus; ii) a severe acute respiratory syndrome corona virus (SARS-CoV); and iii) a Middle East respiratory syndrome corona virus (MERS-CoV).

2. The method of claim 1, wherein said pharmaceutically effective amount is equivalent to a dosage of i) about 0.1 g to 10 g per day; ii) about 1 g to 10 g per day; and/or iii) about 5 g to 10 g per day.

3. The method of claim 1, wherein said 2'-FL i) reduces pathogen binding to cells of said subject; ii) attenuates said pathogen-induced immune response in said subject; and/or iii) modulates host immune response antagonizing said pathogen-induced immune response in said subject.

4. The method of claim 1, wherein said at least one isolated HMO is administered to the lung and/or the GI tract of the subject.

5. The method of claim 1, further comprising administering a pharmaceutically effective amount of an additional agent capable of attenuating, or treating said pathogen-induced immune response and/or promoting recovery from a pathogen-induced immune response to said subject, wherein said additional agent comprises i) another HMO selected from the group consisting of 6'-sialyllactose (6'-SL), 3'-sialyllactose (3'-SL), Lacto-N-tetraose (LNT), Lacto-N-neotetraose (LNnT), 3-fucosyllactose (3-FL), Lacto-N-fucopentaose I (LNF I), Lacto-N-fucopentaose II (LNF II), Lacto-N-fucopentaose HI (LNF ID), Lactodifucotetraose (LDFT), Lacto-N-difucohexaose I (LDFH I), Lacto-N-difucohexaose I] (LDFH ID) and Disialyllacto-N-tetraose (DSLNT); ii) a non-HMO prebiotic agent comprises galacto-oligosaccharides (GOS) or fructo-oligosaccharides (FOS); iii) a non-HMO probiotic agent comprises at least one probiotic bacterium of the genera *Bifidobacterium, Lactobacillus, Lactococcus, Leuconostoc, Pediococcus, Enterococcus, Streptococcus, Bacteroides, Parabacteroides, Prevotella* or *Clostridium*, or iv) the additional agent comprises at least one selected from the group consisting of antibiotics or anti-viral compounds, anti-inflammatory compounds, natural or synthetic corticosteroids, cortisone, hydrocortisone, bethamethasone, prednisone, prednisolone, methylprednisolone, dexamethasone, triamcinolone, non-steroidal anti-inflammatory drugs (NSAIDs), ibuprofen, naproxen, indomethacin, oxaprozin, etodolac, nabumetone, diclofenac, vimovo, anti-pyretics, paracetamol, aspirin, and acetaminophen.

6. The method of claim 1, wherein said composition is in the form of a powder, a tablet, an aerosol, feed for mammalian animals, a packet of sugar, yogurt, a beverage, a weaning food, or an infant formula.

7. The method of claim 1, wherein said subject is a human, a non-human primate, mouse, rat, dog, cat, horse, cattle, sheep, pig, chicken, or goat.

8. The method of claim 1, wherein said subject is an infant, a child, an adult, and/or an elder.

9. The method of claim 1, wherein said subject has or is prone to have a disease or disorder selected from the group consisting of pneumonia, acute respiratory distress syndrome (ARDS), respiratory failure, impaired lung function, hypoxemia, systemic organ failure, infectious diarrhea, antibiotic-associated diarrhea, traveler's diarrhea, necrotizing enterocolitis, inflammatory bowel disease, and an allergy inflammation.

* * * * *